United States Patent
Le Thiesse

(10) Patent No.: US 8,557,380 B2
(45) Date of Patent: Oct. 15, 2013

(54) FORM OF HYDROQUINONE AND PRODUCTION THEREOF

(75) Inventor: Jean-Claude Le Thiesse, Saint-Etienne (FR)

(73) Assignee: Rhodia Operations, Aubervilliers (FR)

( * ) Notice: Subject to any disclaimer, the term of this patent is extended or adjusted under 35 U.S.C. 154(b) by 565 days.

(21) Appl. No.: 12/306,660

(22) PCT Filed: Jun. 27, 2007

(86) PCT No.: PCT/FR2007/001080
§ 371 (c)(1),
(2), (4) Date: Jun. 5, 2009

(87) PCT Pub. No.: WO2008/000956
PCT Pub. Date: Jan. 3, 2008

(65) Prior Publication Data
US 2009/0324952 A1 Dec. 31, 2009

(30) Foreign Application Priority Data
Jun. 29, 2006 (FR) .................................... 06 05868

(51) Int. Cl.
*B32B 5/16* (2006.01)
*C07C 37/68* (2006.01)
*C07C 39/08* (2006.01)

(52) U.S. Cl.
USPC ............ 428/402; 568/715; 568/753; 568/763

(58) Field of Classification Search
USPC ............................ 428/402; 568/716, 753, 763
See application file for complete search history.

(56) References Cited

U.S. PATENT DOCUMENTS

| 1,847,583 | A | * | 3/1932 | Williams ...................... 568/747 |
| 2,881,230 | A | * | 4/1959 | Buell .............................. 62/544 |
| 3,234,307 | A | | 2/1966 | Tuttle |
| 3,953,528 | A | * | 4/1976 | Inada et al. .................... 568/753 |
| 3,960,968 | A | * | 6/1976 | Vernaleken et al. ........... 568/721 |
| 4,308,110 | A | * | 12/1981 | Hosaka et al. ................... 203/48 |
| 5,936,115 | A | * | 8/1999 | Melder et al. .................. 560/189 |
| 6,844,472 | B1 | * | 1/2005 | Bourdon et al. ............... 568/758 |
| 7,235,299 | B2 | | 6/2007 | Le Thiesse |
| 8,071,817 | B2 | * | 12/2011 | Gayet et al. .................... 568/753 |
| 2006/0135730 | A1 | * | 6/2006 | Le Thiesse ....................... 528/86 |
| 2009/0306436 | A1 | * | 12/2009 | Gayet et al. .................... 568/763 |

FOREIGN PATENT DOCUMENTS

| EP | 0740954 A1 | 11/1996 |
| JP | 2000302716 | 10/2000 |

OTHER PUBLICATIONS

Online machine translation of JP 2000-302716, (2000).*
HYdroquinone Premium flakes, Sale brochure from Rhodia Group (circa 2005).*
Hydroquinone flakes, Sale brochure from Shantou Risun Co., Ltd (circa 2005).*
Eastman, Product Data Sheet, Apr. 2001.*

* cited by examiner

*Primary Examiner* — Hoa (Holly) Le
(74) *Attorney, Agent, or Firm* — Dentons US LLP

(57) ABSTRACT

Novel hydroquinone flakes are prepared from a powder thereof, by, if necessary, melting the hydroquinone powder, depositing the hydroquinone in the liquid state as a film on a support made of a material or coated with a material which conducts heat, solidifying the hydroquinone by adjusting the support to an appropriate temperature, and recovering the solidified product in the form of flakes.

8 Claims, 4 Drawing Sheets

FORM OF HYDROQUINONE AND PRODUCTION THEREOF

CROSS-REFERENCE TO PRIORITY/PCT APPLICATIONS

This application claims priority under 35 U.S.C. §119 of FR 0605868, filed Jun. 29, 2006, and is a continuation/national phase of PCT/FR 2007/001080, filed Jun. 27, 2007 and designating the United States (published in the French language on Jan. 3, 2008, as WO 2008/000956 A1; the title and abstract were also published in English), each hereby expressly incorporated by reference in its entirety and each assigned to the assignee hereof.

A subject matter of the present invention is a new form of hydroquinone.

More specifically, a subject matter of the invention is hydroquinone flakes. The invention also relates to the preparation of said flakes.

Hydroquinone is a product widely used in numerous fields of application as polymerization inhibitor or antioxidant in elastomers. Another field of application is photography. It follows that this is a staple product.

Hydroquinone is currently available commercially in the form of a powder formed of small and brittle needles. The disadvantages which result therefrom are the presence of fines, which cause problems of dust formation during storage and handling of said powder.

In point of fact, hydroquinone dust is not without danger with regard to the environment, due to the risks of explosion, and with respect to man, as this substance is irritating to the eyes and to the respiratory tract and can also cause irritation to the skin when it is brought into contact with the latter.

Provision has been made, according to JP-A-2002-302716, to formulate hydroquinone in the form of granules according to a granulating technique which consists in passing the hydroquinone powder between two rolls, making it possible to obtain blocks, and in then crushing these blocks, so as to obtain said granules.

Another forming described in EP-A 1 556 322 consists in forming the hydroquinone as beads, that is to say highly spherical solid particles, which are devoid of dust and which have a physical form which confers on them good resistance to attrition.

The size of the particles, expressed by the median diameter ($d_{50}$), is between 300 μm and 2000 μm, preferably between 500 μm and 1500 μm. The median diameter is defined as being such that 50% by weight of the particles have a diameter of greater than or less than the median diameter.

The process for the preparation of said beads consists in preparing, under hot conditions, a concentrated aqueous solution of hydroquinone, in then fragmenting the solution into droplets by passing through a nozzle and in cooling the droplets obtained in a gas stream so that they solidify to give beads which are subsequently recovered and dried.

The said process concerns the prilling technique but, contrary to what is normally employed, it does not consist in melting the hydroquinone and in subsequently fragmenting it by passing through a nozzle.

This is because the difficulty with which a person skilled in the art was confronted was that hydroquinone melts at a high temperature of 172° C. and, furthermore, hydroquinone has a very high vapor pressure (greater than 25 mbar at this temperature), which results, at the nozzle outlet, in phenomenal evaporation, resulting in problems of dust and of decontamination which are absolutely unacceptable from an industrial viewpoint.

Thus, the process provided by EP-A 1 556 322 is to prepare hydroquinone beads according to the prilling technique by starting from an aqueous hydroquinone solution.

The beads obtained according to EP-A 1 556 322 are high quality products in terms of absence of dust and of flowability.

The disadvantage of this process is related to the prilling, which still requires a high capital cost with regard to the operational capacity and which subsequently involves an additional stage of drying the beads obtained.

The object of the present invention is to provide a new form or a new presentation of hydroquinone which makes it possible to overcome the above-mentioned disadvantages.

A subject matter of the present invention is a new form of hydroquinone existing under the appearance of flakes.

More specifically, the new form of hydroquinone is provided under the appearance of large particles which have a platelet shape; these particles being known as "flakes".

The platelet particles correspond to a general shape factor defined in the plane by a highly varied outline which can be more or less square, rectangular, round or oval.

The various flakes of varied shape are inscribed within a parallelepiped exhibiting the dimensions specified below.

The length generally varies between 0.5 and 6 cm, preferably between 1 and 3 cm.

For its part, the width ranges between 0.5 and 3 cm, preferably between 0.5 and 1.5 cm.

The measurements are carried out on a sample of 20 flakes withdrawn at random.

The length and the width are determined by measurement using a graduated ruler.

The abovementioned parallelepipeds have one of their three dimensions (the thickness) much smaller than the other two (width and length).

As regards the thickness, it is between 400 μm and 1500 μm, preferably between 500 and 750 μm.

The thickness is measured using a sliding caliper or a Palmer device.

It should be noted that it is not out of the question for some particles to exhibit dimensions outside the limits given above.

FIG. 1 represents a photograph taken using a digital camera which shows the morphology of flake type of the hydroquinone obtained according to the invention.

It should be emphasized that these large particles exhibit clean-cut edges.

Figure 1:
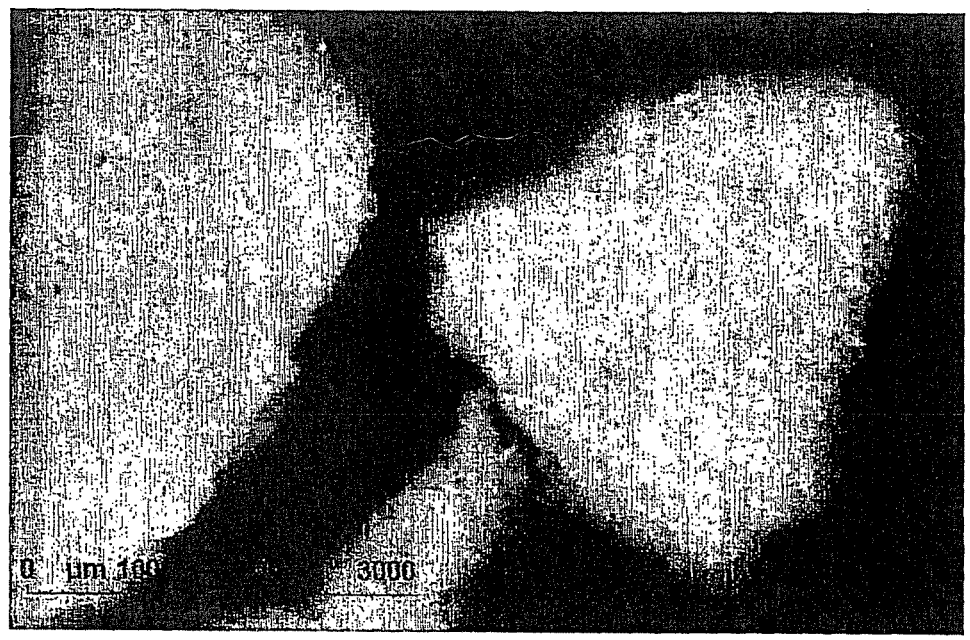
Figure 2:
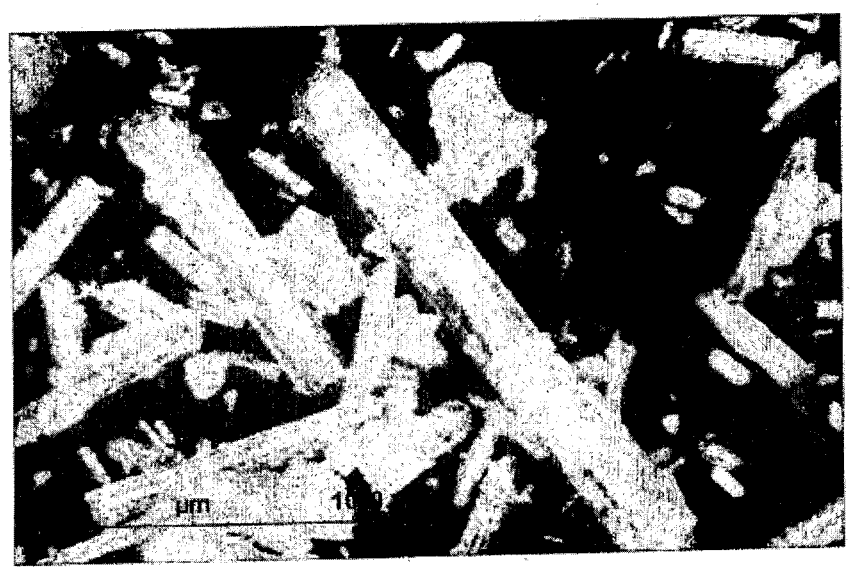
FIG. 2 represents a photograph taken using a digital camera which shows the morphology as needles of the crystals of the hydroquinone powder available commercially.

One characteristic of the product of the invention is a very low level of fine particles in comparison with a presentation in the powder form.

The level of the fine particles is defined as the percentage by weight of the particles with dimensions of less than 100 μm.

Particles which pass through a sieve having a mesh size of 100 μm are regarded according to the invention as fine particles.

The level of the fine particles is less than 3% by weight, preferably between 0.7 and 1.5% by weight and more preferably between 0.7 and 1% by weight.

It will be specified, by way of indication, that the size of the fine particles ranges between 1 μm and 100 μm, with a median diameter lying between 20 and 30 μm.

The median diameter is defined as being such that 50% by weight of the particles have a diameter greater than or less than the median diameter.

By way of comparison, it will be mentioned that the level of the fine particles of the hydroquinone in the powder form is of the order of 20% by weight, which means that the content of the fine particles (or dust) is divided by 10, indeed even by 20.

In order to define the particle size of the product of the invention, the percentage by weight of the particles with dimensions of less than 2.5 mm, that is to say particles which pass through a sieve having a mesh size of 2.5 mm, is also defined.

This content is generally between 20 and 40% by weight.

By way of a comparison, it will be mentioned that 100% of the particles of hydroquinone in the powder form are less than 2.5 mm.

The hydroquinone flakes have a density which can be more or less high. The (loose) bulk density of the flakes is preferably at least 0.4 g/cm$^3$ and is more preferably between 0.4 and 0.6 g/cm$^3$ and generally between 0.45 and 0.55 g/cm$^3$.

The (tapped) bulk density of the flakes is preferably at least 0.5 g/cm$^3$ and is more preferably still between 0.5 and 0.8 g/cm$^3$ and generally between 0.6 and 0.7 g/cm$^3$.

The densities are measured on an undried product according to the test described in the European Phatmacopeia standard [Volume 1, p. 256 (2004), 5th edition], with the only difference that the 250 ml of test specimen is replaced by a 1 liter test specimen.

The invention thus lies in a new forming of the hydroquinone which, although having a physical form which allows it to withstand attrition, retains a rate of dissolution compatible with subsequent use.

Thus, the rate of dissolution of the flakes varies according to the thickness of said flakes.

The dissolution time in water of an amount of flakes necessary in order to obtain a final concentration of hydroquinone in the solution of 4.8% by weight varies between 10 and 30 min, depending on the thickness of the flakes.

These measurements correspond to a test which consists in measuring the time necessary to dissolve said amount in water maintained at ambient temperature (20° C.) and kept stirred, for example using a propeller stirrer with 4 inclined blades.

A similar test is carried out in order to determine the rate of dissolution of the flakes in acrylic acid.

The test consists in defining the time necessary to dissolve the amount of flakes necessary in order to obtain a final concentration of hydroquinone in the acrylic acid of 2% by weight.

This rate ranges between 30 min and 1 h, depending on the thickness of the flakes.

Measured under the same conditions, the rates of dissolution of the hydroquinone powder in water and in acrylic acid are 9 min and 20 min respectively.

It should be noted that the dissolution times of the hydroquinone formed according to the invention are slightly increased, but this increase is acceptable to the user in view of the advantages otherwise obtained.

The novel structure of the products of the invention is obtained by virtue of a perfectly adapted manufacturing process.

The process of the invention for the preparation of the hydroquinone flakes comprises the following stages:
  if necessary melting the hydroquinone powder,
  depositing the hydroquinone in the liquid state as a film on a support made of a thermally conductive material or coated with a thermally conductive material,
  solidifying the hydroquinone by bringing the support to the appropriate temperature,
  recovering the solidified product in the form of flakes using any appropriate means.

According to a preferred embodiment of the invention, the oxygen is removed beforehand from the chamber in which the forming operation is carried out.

Thus, the forming of the hydroquinone in the liquid state is carried out in an atmosphere freed from oxygen. According to one embodiment of the invention, an atmosphere of inert gases is established in the chamber. Recourse may be had to a noble gas, preferably argon, but it is generally preferable to use nitrogen due to its lower cost.

Once the inert atmosphere has been established, the hydroquinone in the liquid state is deposited as a film on an appropriate support.

It is possible to envisage directly feeding the hydroquinone in the liquid state originating from a manufacturing line.

It is also possible to provide a stage of the process of the invention which consists in melting the hydroquinone. To this end, the product is heated to its melting point. Preferably, the product is brought to a temperature slightly greater than its melting point of 172.5° C., preferably greater by at most 10° C. with respect to its melting point. The temperature to which the hydroquinone is brought is chosen between 178° C. and 185° C.

This operation is generally carried out with stirring.

The operation can be carried out in a stirred and heated tank. Heating is advantageously carried out by circulation of steam or an appropriate heat-exchange fluid in the jacket.

Mention may in particular be made, as heat-exchange fluids suitable for the invention, of heavy esters of carboxylic acids (for example, octyl phthalate), aromatic ethers, such as diphenyl ether and/or benzyl ether, biphenyl, terphenyls, the other optionally partially hydrogenated polyphenyls, paraffinic and/or naphthenic oils, petroleum distillation residues, silicone oils, and the like.

In accordance with the process of the invention, the hydroquinone in the liquid state is deposited as a film on a support made of a thermally conductive material or coated with a thermally conductive material.

Recourse is had, for the choice of the material, to any material which does not react with hydroquinone.

Furthermore, as this material has the property of conducting heat, the choice is advantageously made of a metal having a thermal conductivity of at least 10 W/m·K, preferably between 15 and 400 W/m·K. It should be noted that the upper limit does not exhibit any critical nature.

Mention may be made, as examples of materials corresponding to the abovementioned characteristics which are entirely well suited to the implementation of the process of the invention, inter alia, of stainless steels.

The choice is advantageously made of stainless steels, such as austenitic steels and more particularly stainless steels 304, 304 L, 316 or 316 L.

Use is made of a steel having at most 22% by weight of nickel, generally between 6 and 20% by weight, preferably between 8 and 14% by weight.

The 304 and 304 L steels have a nickel content varying between 8 and 12% and the 316 and 316 L steels have a nickel content varying between 10 and 14%.

Such steels are commonly used industrially.

Reference may be made, for the definition of austenitic steels, to the work by Robert H. Perry et al. [Perry's Chemical Engineers' Handbook, Sixth Edition (1984), pages 23-44].

The process of the invention is carried out using a device which makes possible the solidification of the hydroquinone in the liquid state on a cooled surface consisting of a conductive material or coated with a conductive material which can be in the form of a conveyor belt, of one or more turntable(s) or else of a rotating cylinder.

The proportions of the equipment come within the competence of a person skilled in the art.

The characteristics of the conveyor belt can vary widely. Thus, the length can range, for example, between 50 cm and 2 m and the width between 1 and 5 m. As regards the rate of forward progression of the belt, it can advantageously vary between 1 m/min and 20 m/min.

The thickness of the flakes is determined by controlling the feed rate of the hydroquinone and the rate of forward progression of the belt.

As regards the turntables, their diameter is generally between 150 and 400 mm.

Their rotational speed is preferably chosen between 5 and 50 revolutions/min.

According to a first alternative form of the invention, the hydroquinone in the liquid state is deposited on a belt or on one or more turntables by spraying via a nozzle and more commonly by an overflow system comprising a feed trough continuously filled with hydroquinone in the liquid state so as to cause the hydroquinone to overflow, which hydroquinone falls by gravity onto the belt or turntable(s).

The hydroquinone is solidified by cooling at a temperature advantageously of between 20° C. and 80° C.

Cooling is generally provided by spraying cold water onto the internal face of the belt, which is not covered with the hydroquinone.

With regard to the turntable(s), they are generally composed of a jacket in which a cooling liquid, preferably water introduced at the appropriate temperature, circulates.

The hydroquinone is recovered in the form of flakes by virtue of a scraper blade.

According to another alternative form of the process, which is preferred, the hydroquinone in the liquid state is deposited on a rotating cylinder.

The cylinder has dimensions which can vary widely.

Thus, the diameter can range from 0.15 to 2.5 m, preferably from 1 to 1.5 m, and the length can vary, for example, between 0.25 and 5 m, preferably 0.5 and 2 m.

The cylinder can be fed in multiple ways.

The cylinder being placed, for example, in 1 to 10 cm of hydroquinone in the liquid state placed in a feed trough, deposition on the cylinder is carried out by dipping.

The cylinder rotates and carries away a thin layer of product which solidifies on the cylinder by cooling.

The cylinder rotates at a speed which is chosen according to the desired thickness of the flakes and the temperature of the feeding.

The layer will become thinner as the rotational speed increases.

The feeding of the hydroquinone in the liquid state can be carried out on the cylinder via an applicator roll, itself fed with hydroquinone in the liquid state.

The feeding can also be carried out on the cylinder by pouring by gravity or via a pump.

The cylinder is cooled by circulating water in a jacket or by spraying water inside the cylinder.

According to one characteristic of the process of the invention, the cylinder is preferably maintained at a temperature of between 20° C. and 80° C. and more preferably between 30° C. and 80° C.

The rotational speed of the cylinder advantageously varies between 0.5 and 20 revolutions/min, preferably between 3 and 6 revolutions/min.

The hydroquinone is maintained on the cylinder for a sufficient length of time for it to solidify.

Subsequently, the formed hydroquinone is recovered using any appropriate means and more particularly using a blade which scrapes the cylinder and detaches the layer of product, which is recovered by any known means, for example by gravity in a recovery tank.

Thus, a preferred embodiment of the process of the invention for the preparation of the hydroquinone flakes comprises the following stages:

freeing from oxygen the chamber in which the forming operation is carried out, if necessary melting the hydroquinone powder, depositing the hydroquinone in the liquid state as a film on a cylinder maintained at a temperature of between 20° C. and 80° C., maintaining the hydroquinone on the cylinder for a sufficient length of time for it to solidify, recovering the solidified product using any appropriate means.

The hydroquinone is obtained in the form of flakes corresponding to the characteristics given above.

The invention does not exclude an additional stage which makes it possible to grade the product obtained.

Thus, the flakes can be introduced, for example, into a blade or bar granulator which makes it possible to reduce the size of the particles in order to have a more homogeneous distribution in the three dimensions and to thus obtain hydroquinone in the form of isotropic particles.

The term "isotropic particles" is understood to mean particles with three equivalent dimensions.

The particles obtained approach the cubic shape and exhibit a size which can vary between 400 and 1500 µm, preferably between 500 and 750 µm.

Thus, the flakes can be used as intermediate in order to manufacture hydroquinone in the form of isotropic particles.

The hydroquinone thus obtained exhibits an increased density.

The following examples illustrate the invention without, however, limiting it.

EXAMPLES

Figure 3:
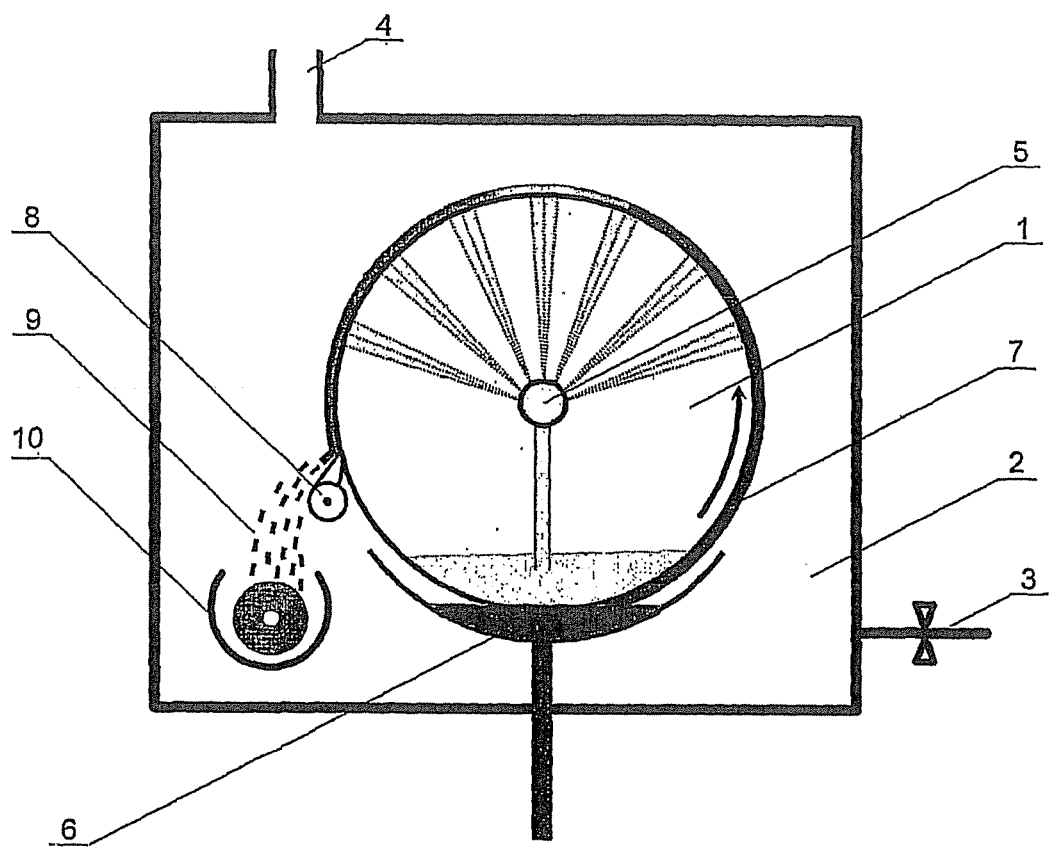
FIG. 3 shows an example of how the process for producing the purified hydroquinone using equipment described in an example.

The process of the invention can be carried out in the equipment described below and represented diagrammatically by FIG. 3.

The hydroquinone flakes are obtained by solidifying hydroquinone in the liquid state on a rotating cylinder 1 made of stainless steel (316) in a chamber 2 in which an atmosphere depleted in oxygen is established by the introduction of nitrogen 3. The gas laden with hydroquinone vapors is discharged from the chamber in the direction of a gas treatment device 4.

The temperature of the cylinder is regulated by spraying water over its internal face 5. There is no direct contact between the cooling water and the product.

The hydroquinone in the liquid state is introduced into a feed tank 6, the temperature of which is regulated by a jacket in which a heat-exchange fluid circulates. The cylinder dips into the molten hydroquinone and, due to its rotation, carries away, at its external surface, a film of molten product 7.

On contact with the cold metal, this film of product gradually solidifies to arrive solid at a scraping blade 8 which detaches it from the cylinder in the form of flakes 9.

The flakes thus obtained are collected in the trough of a screw conveyor 10 which removes them from the chamber.

The main parameters influencing the productive output and the thickness of the flakes produced are:

the rotational speed of the cylinder, S, the temperature of the cooling water, Tw, the depth of immersion of the cylinder in the molten product, D, the temperature of the molten product, Tp.

By way of examples, with a cylinder with a surface area of 0.75 m² (length=0.48 m; diameter=0.50 m), the results summarized in table (I) below are obtained.

The physicochemical characteristics of the flakes obtained are also given in table (I).

TABLE I

| Example No. | 1 | 2 | 3 | 4 | 5 |
| --- | --- | --- | --- | --- | --- |
| S (revolutions/minute) | 2 | 4 | 4 | 6 | 10 |
| Tw (° C.) | 60 | 80 | 40 | 60 | 40 |
| D (mm) | 25 | 25 | 25 | 40 | 40 |
| Tp (° C.) | 180 | 180 | 180 | 185 | 185 |
| Productive output (kg/h) | 98 | 126 | 146 | 181 | 281 |
| Thickness of the flakes (mm) | 0.95 | 0.65 | 0.75 | 0.65 | 0.60 |
| % by weight of particles passing through a sieve with a mesh size of 100 μm | 0.8% | 0.7% | 0.9% | 0.8% | 0.9% |
| Loose bulk density (g/cm³) | 0.52 | 0.47 | 0.48 | 0.46 | 0.53 |
| Tapped bulk density (g/cm³) | 0.70 | 0.65 | 0.67 | 0.61 | 0.66 |
| Dissolution time in water at 20° C. (production of a 4.8% by weight solution) | 21 min | 15 min | 18 min | 14 min | 14 min |
| Dissolution time in acrylic acid at 20° C. (production of a 2.0% by weight solution) | 45 min | 30 min | 35 min | 30 min | 30 min |

The photograph in FIG. 1 illustrates the morphology of the product obtained according to example 5. A general view of the product of example 5 is given by FIG. 4.

What is claimed is:

1. Flakes of hydroquinone, comprising particles having a platelet shape and having a length ranging from 0.5 to 6 cm, a width ranging from 0.5 to 3 cm and a thickness ranging from 400 μm to 1,500 μm, said flakes having a level of fine particles, particles having dimensions of less than 100 μm, of less than 3% by weight thereof, wherein said flakes are formed by depositing hydroquinone in a molten liquid state as a film on a support made of a thermally conductive material or coated with a thermally conductive material, solidifying the hydroquinone by bringing the support to the appropriate temperature, recovering the solidified product in the form of flakes using any appropriate means.

Figure 4:
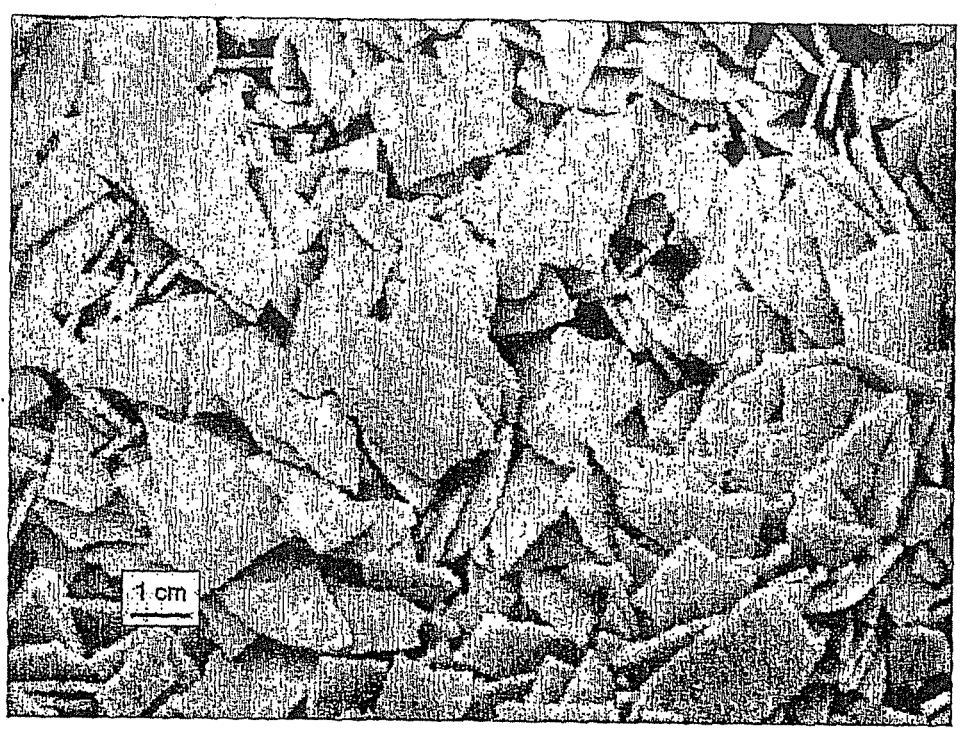
FIG. 4 represents a photograph, also taken using a digital camera, which shows a better general view of the product of the invention by virtue of a smaller magnification shown on the photograph.

2. The hydroquinone flakes as defined by claim 1, having a morphology as shown in FIG. 1 or FIG. 4.

3. The hydroquinone flakes as defined by claim 1, wherein from 20% to 40% of the particles, by weight, are able to pass through a sieve having a mesh size of 2.5 mm.

4. The hydroquinone flakes as defined by claim 1, having a (loose) bulk density of the flakes of at least 0.4 g/cm³.

5. The hydroquinone flakes as defined by claim 1, having a (tapped) bulk density of the flakes of at least 0.5 g/cm³.

6. The hydroquinone flakes as defined by claim 1, having a length ranging from 1 to 3 cm.

7. The hydroquinone flakes as defined by claim 1, having a thickness ranging from 500 to 750 μm.

8. The hydroquinone flakes as defined by claim 1, having a level of fine particles ranging from 0.7 to 1% by weight thereof.

* * * * *